United States Patent [19]

Gorsuch et al.

[11] Patent Number: 5,151,082
[45] Date of Patent: * Sep. 29, 1992

[54] APPARATUS AND METHOD FOR KIDNEY DIALYSIS USING PLASMA IN LIEU OF BLOOD

[75] Inventors: Reynolds G. F. Gorsuch, Yountville; John Atkin, Corona Del Mar, both of Calif.

[73] Assignee: Heathdyne, Inc., Atlanta, Ga.

[ * ] Notice: The portion of the term of this patent subsequent to Aug. 21, 2007 has been disclaimed.

[21] Appl. No.: 570,009

[22] Filed: Aug. 20, 1990

Related U.S. Application Data

[63] Continuation-in-part of Ser. No. 229,007, Aug. 5, 1988, Pat. No. 4,950,224.

[51] Int. Cl.⁵ .......................................... H61M 37/00
[52] U.S. Cl. .......................................... 604/4; 604/6; 604/53; 210/645
[58] Field of Search .......................... 604/4–8, 604/52, 53, 405, 406, 20, 26; 210/645, 646

[56] References Cited

U.S. PATENT DOCUMENTS

| | | | |
|---|---|---|---|
| Re. 31,688 | 9/1984 | Popovich et al. | 604/4 |
| 4,240,907 | 12/1980 | Bentley | 210/646 |
| 4,559,034 | 12/1985 | Kirita et al. | 604/52 |
| 4,563,170 | 1/1986 | Aigner | 604/43 |
| 4,583,969 | 4/1986 | Mortensen | 604/4 |
| 4,631,053 | 12/1986 | Taheri | 604/4 |
| 4,767,400 | 8/1988 | Miller et al. | 604/8 |

Primary Examiner—Robert A. Hafer
Assistant Examiner—Kerry Owens
Attorney, Agent, or Firm—Jones, Askew & Lunsford

[57] ABSTRACT

Kidney dialysis in which metabolic waste products are removed from plasma instead of blood. Plasma separation takes place in vivo through a filter implanted within a blood vessel, and the separated plasma is removed to an extracorporeal dialysis apparatus for separating waste products from the plasma. The plasma then is returned to the bloodstream. Plasma flow in the system is significantly less than blood flow used in current hemodialysis systems, so that the present system performs dialysis continuously in real time to eliminate the extreme swings of toxicity associated with high-volume hemodialysis.

11 Claims, 3 Drawing Sheets

A: UREASE
B: ZEOLITE
C: ELECTROLYE
   EQUILIBRIUM

APPARATUS AND METHOD FOR KIDNEY DIALYSIS USING PLASMA IN LIEU OF BLOOD

CROSS-REFERENCE TO RELATED INVENTION

This is a continuation-in-part of Ser. No. 229,007 filed Aug. 5, 1988, U.S. Pat. No. 4,950,224.

FIELD OF INVENTION

This invention relates in general to treatment of renal disease, and relates in particular to an apparatus and method for dialysis in real time using plasma in lieu of blood.

BACKGROUND OF THE INVENTION

End stage renal disease currently affects over 100,000 patients in the United States, and over 400,000 patients worldwide. The patient load for this disease continues to grow at a seven percent annual rate.

Kidney failure may be acute or chronic. Acute failure may be caused by trauma, surgery, or disease but is time-limited as the patient heals. Chronic failure is permanent and will continue for the long term until the patient dies. Treatment for chronic or end stage renal disease consists of kidney transplant procedures or dialysis. Kidney transplant therapy is limited by the availability of suitable organ donors, and dialysis becomes the only remaining treatment for chronic kidney failure.

Dialysis is the process of removing metabolic waste products from the blood, a function performed by the natural kidney in a healthy condition. These waste products include salts, urea, creatinine, uric acid, and water. The substances are removed by diffusion across a membrane to a dialysate fluid which has a low concentration of the substances.

Dialysis takes place either by continuous ambulatory peritoneal dialysis in which the membrane used is the vascular membranes of the body in the peritoneal cavity, or hemodialysis in which an artificial membrane is used. In hemodialysis, blood is removed from an artery or vein, passed over one side of an extracorporeal porous dialyzer membrane is used. In hemodialysis, blood is removed from an artery or vein, passed over one side of an extracorporeal porous dialyzer membrane, and returned to the body via a vein. The membrane is made of cellulous or another suitable material. Dialysate fluid is passed over the other side of the dialyzer membrane and the metabolic waste products pass through the porous membrane from the blood to the dialysate by the process of diffusion. The pores in the membrane are sized such that the waste products pass through the membrane but other blood components such as hemoglobin, albumin, gamma globulin, virus and bacterial bodies, are too large and cannot pass through the pores. Excess water is passed through the membrane by an ultrafiltration process in which a positive pressure gradient is created between the blood and the dialysate on opposite sides of the membrane.

Although hemodialysis is widely used as a treatment for chronic kidney failure, there are significant problems associated with that procedure. For one, the removal of whole blood from the body, followed by processing and returning that blood, causes clotting, infection, and damage to the cells, as well as damage to proteins and other blood components.

The batch-treatment orientation of hemodialysis represents another problem. Current hemodialysis therapy methods are high velocity, high volume batch processes where the total blood volume of a patient is removed, dialyzed, and returned in a single treatment session which may last three to four hours. These treatment sessions take place several times each week. Because the generation of toxic metabolic waste by the body is continuous, this waste will build up to unacceptable concentrations in the blood between dialysis sessions. Furthermore, the massive blood removal and constituent changes during a dialysis session cause cardiovascular trauma as well as nausea and other systemic disorders.

Patient immobility is yet another problem of present hemodialysis methods. Because of the large volume, high flow requirements of present hemodialysis systems, the apparatus is large and heavy and the patient thus is immobilized for the time that the procedure requires.

SUMMARY OF THE INVENTION

Stated generally, the present invention recognizes that the metabolic waste products to be removed are carried by the blood plasma. Consequently, dialysis can take place according to the present invention by removing plasma from the blood, dialyzing the plasma to remove the waste products, and returning the dialyzed plasma to the bloodstream thus avoiding damage to other components of the blood. Furthermore, the volume of fluid processed according to the present invention preferably is substantially reduced if only plasma is processed, thereby simplifying the dialysis apparatus.

Stated in somewhat greater detail, plasma is separated in vivo from other blood components through a membrane implantable in a blood vessel and functioning as a filter to admit plasma while preventing other blood components from passing through the membrane. The plasma thus separated in vivo by the membrane then is removed from the body and dialyzed to extract toxic metabolic waste.

In vivo separation of plasma preferably is accomplished by apparatus comprising one or more microporous hollow fibers implantable in a blood vessel and having a pore size sufficient to admit plasma while preventing other blood components from entering the hollow interior of the fiber. The separated plasma is transported to the exit lumen of a catheter which conducts the plasma to an extracorporeal dialysis apparatus. Only plasma, but not cellular or other components of blood, is removed for dialysis and returned to the bloodstream, thus eliminating the damage to other blood components caused by current hemodialysis methods.

The system of the present invention processes plasma and performs dialysis continuously in real time, as does the natural healthy kidney, thus eliminating the extreme swings of toxicity, blood volumes, and blood composition induced by current hemodialysis processes. Plasma flow in a preferred system according to the present invention is approximately 7.5 ml/min as contrasted with the 250-300 ml/min used in previous hemodialysis systems. Moreover, the relatively low flow rate of the present invention permits the entire apparatus to be downsized and thus made small enough to be portable and ambulatory. Thus, the patient can pursue other activities while dialysis is taking place.

Accordingly, it is an object of the present invention to provide an improved apparatus and method for treatment of end stage renal disease.

It is another object of the present invention to provide an improved apparatus and method for kidney dialysis.

It is a further object of the present invention to remove metabolic waste products from the bloodstream by cascade filtration including in vivo separation of plasma from cellular components of blood, followed by extracorporeal removal of waste products from the separated plasma.

It is still another object of the present invention to provide an apparatus and method for accomplishing kidney dialysis continuously in real time.

It is a yet further object of the present invention to provide an apparatus and method for kidney dialysis which is small enough to enable the patient to remain ambulatory while dialysis is taking place.

Other objects and advantages of the present invention will become more readily apparent from the following description of preferred embodiments.

DETAILED DESCRIPTION OF PREFERRED EMBODIMENTS

Figure 1:
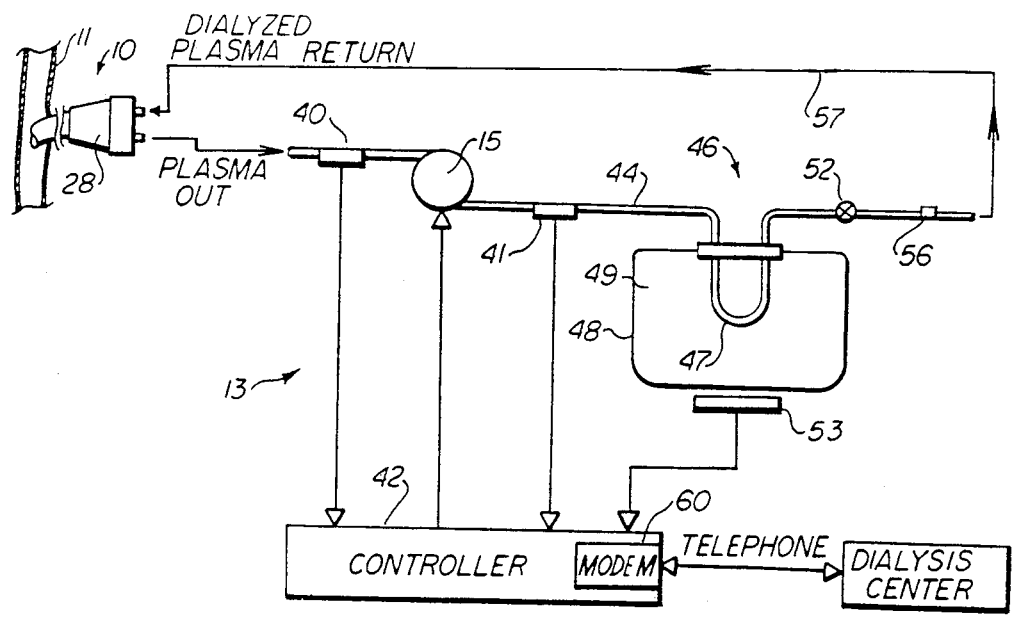
FIG. 1 is a partially schematic view showing a first preferred embodiment of the present invention including an apparatus for in vivo separation of plasma and a first embodiment of a continous dialysis apparatus.
Figure 6:
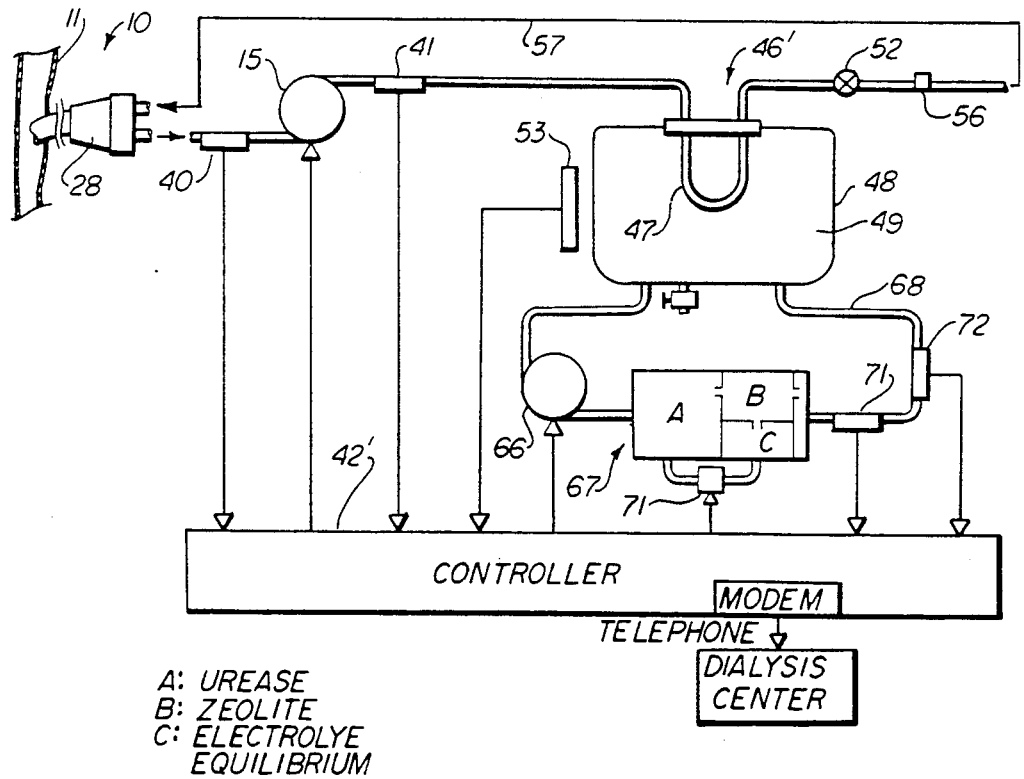
FIG. 6 is a partially schematic view showing another embodiment of the present invention including the plasma separation apparatus shown in FIG. 2 and a second embodiment of dialysis apparatus.

Turning first to FIG. 1 for an overview of the invention, 10 generally denotes a plasma separation apparatus shown inserted in a vein 11 of a patient undergoing dialysis according to the present invention. The plasma separation apparatus 10 functions as a primary filter to separate plasma from the cellular products of blood flowing through the vein 11, and the separated plasma leaves the patient through the plasma exit tube 12 connected to the plasma separation apparatus 11. The plasma exit tube 12 conducts the separated plasma to the dialysis apparatus 13 where metabolic waste products are separated from the plasma in a manner described below in greater detail. A plasma return tube 14 connects to the plasma outlet of the dialysis apparatus 13 and conducts the dialyzed plasma back to the plasma separation apparatus 10, where the dialyzed plasma is reintroduced to the patient's bloodstream within the vein 11. A pump 15, preferably a peristaltic pump or the like, provides positive displacement of the dialyzed plasma to the dialysis apparatus 13. It will thus be appreciated that the plasma separation apparatus 10 functions as an in vivo primary filter to separate plasma from the blood, and that the dialysis apparatus 13 functions as a secondary filter in cascade with the primary filter for removal of waste products from the separated plasma.

Figure 2:
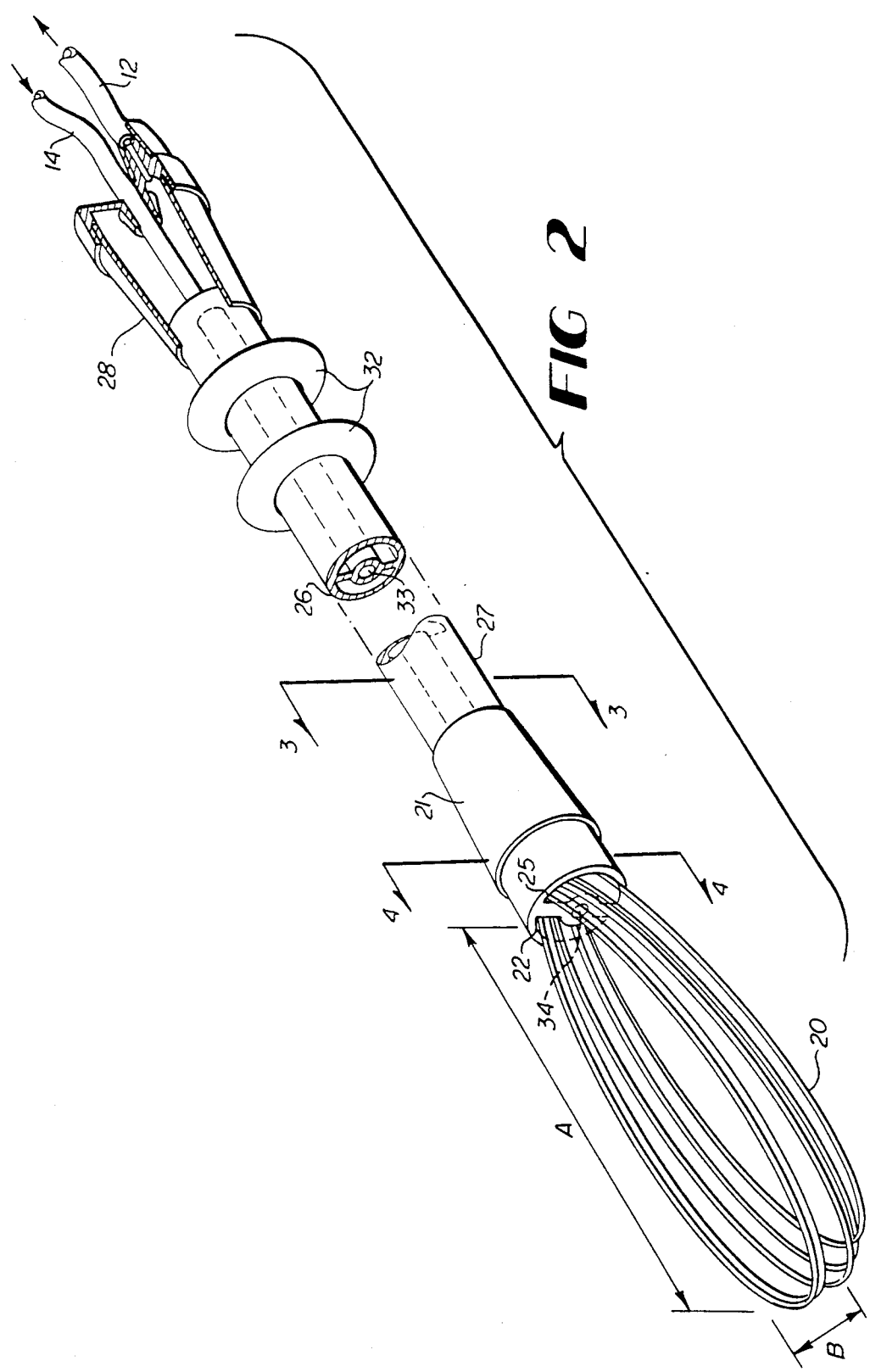
FIG. 2 is an enlarged pictorial view, partially broken away for illustrative purposes, showing the in vivo plasma separation apparatus.

Details of the plasma separation apparatus 10 are shown in FIG. 2. The in vivo plasma separation apparatus 10 comprises at least one and preferably a plurality of hollow microporous fibers 20 each having a hollow interior disposed longitudinally therein. The fibers 20 can be made of any suitable material such as polymeric plastic, but are preferably polymeric polypropylene. The fibers 20 can be made by methods known to those skilled in the art. For example, polypropylene can be mixed with a solvent and the mixture spun; as the solvent and polymer phase are separated the fiber is formed. One suitable fiber commercially available is Plasmaphan ® membranes made from polypropylene polymer (ENKA AG, Wuppertal, West Germany). The fibers 20 possess a microporous structure having a very high void volume, low variation in pore distribution, and high reproducibility in production. The fiber pore size is sufficient to admit plasma to pass through the wall of the hollow fiber and into the hollow center of the fiber, although the overall size of the fibers should not significantly obstruct fluid flow through the blood vessel. Cellular components of the blood, however, are unable to diffuse through the fiber pores. Predominantly large molecules will pass around the apparatus 10 within the vein fluid flow. The vein fluid flow also prevents clogging of the pores. The fiber pore size can be from about 0.1 to 1.0 $\mu$m; preferably, from about 0.2 to 0.8 $\mu$m; and more preferably, from about 0.4 to 0.6 $\mu$m.

The fibers 20 are longitudinally aligned in a generally parallel or radial orientation. The plurality of fibers 20 provide a large available surface area through which plasma can diffuse. The individual fibers can be arranged in a bundle to ensure adequate fluid-membrane contact along substantially the entire exterior surface of the membrane. The fibers 20 preferably are loosely bundled so as to improve surface area contact with blood.

Figure 4:
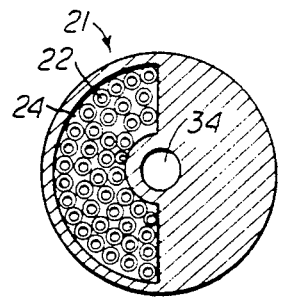

The fibers 20 constitute the active element of the plasma separation apparatus 10. Each individual fiber 20 defines a generally elongated loop extending outwardly from the distal header 21 to which the fibers are connected. The fibers 20 are connected to the distal header 21 by standard potting and cutoff techniques used in the medical industry in the manufacture of hollow fiber oxygenators and hollow fiber kidney dialysis membrane filters, for example. In this process, the fibers are potted into a solid block of plastic or epoxy, fixing their position, and the block then is cut transverse to the fibers to expose their open ends to a chamber for gas or fluid access. The connected fibers 20 describe a generally circular pattern at the distal header 21, as seen in FIG. 2. However, in the disclosed embodiment only one end 22 of each fiber 20 remains open to fluid flow communication with the manifold chamber 24 within the distal header 21, as shown in FIG. 4. That manifold chamber 24 occupies approximately half the circular arc of the distal header 21, and in turn is in fluid flow communication with an outer lumen 26 of the triple-lumen catheter 27 connected between the distal header 21 and the proximal header 28, FIG. 2. Each fiber 20 thus describes a loop commencing at one end 22 open to the manifold chamber 24 within the distal header 21, and terminating at the other end 25 which is closed within the potted distal header. The full length of the hollow interior in each fiber 20 thus is in fluid communication with the outer lumen 26 of the catheter 27.

Figure 5:
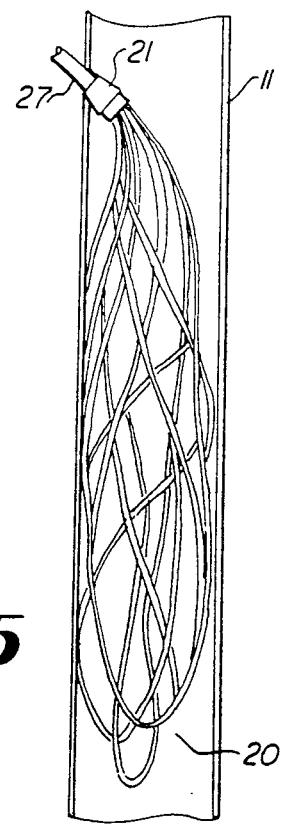
FIG. 5 is a section view of the apparatus shown in FIG. 2 when implanted in a blood vessel.

The portion of the plasma separation apparatus 10 inserted into the vein 11 includes the active elements made up of the fibers 20 and the distal header 21, as illustrated in FIG. 5. The techniques for placing the plasma separation apparatus 10 in a suitable vein are described in detail in U.S. Pat. No. 4,950,224, which is incorporated herein by reference. The catheter 27 extends outwardly from the distal header 21 to the proximal header 28, from which the plasma exit tube 12 and the plasma return tube 14 connect the plasma separation apparatus 10 to the dialysis apparatus 13 as shown in FIG. 1. A pair of anti-bacteria barriers 32 are located surrounding the catheter 27 adjacent the proximal header 28 to prevent infection near the exit of the catheter from the skin. The ringlike barriers 32, which can be greater or fewer in number than two, are made of a nonreactive porous material having a relative uniform pore size sufficient to prevent bacteria from passing through the barriers yet permitting smaller molecules to pass therethrough. The porous nature of the barriers 32 also promotes ingrowth of body tissue for anchoring the implanted catheter 27 within the body.

Figure 3:
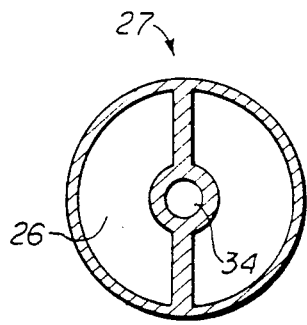
FIGS. 3 and 4 are section views taken perspectively along lines 3—3 and 4—4 of FIG. 1.

The catheter 27, as mentioned previously, is a triple-lumen catheter having an axial center lumen 33 surrounded by a pair of outer lumens. One outer lumen 26 is connected to the manifold chamber 24 in communication with the open ends 22 of the fibers 20; the other outer lumen of the triple-lumen catheter is not used in the disclosed embodiment. The center lumen 33 is connected at the proximal header 28 to the plasma return tube 14, and extends through the distal header 21 to the plasma return outlet 34 (FIGS. 2 and 3) located between the open ends 22 and closed ends 25 of the fibers 20.

Plasma transfer through the fibers 20 is accomplished within the vein 11 as blood flowing through the vein comes in contact with the porous fibers. Plasma fluid and dissolved molecules are sufficiently small to diffuse through the membrane of the fibers 20 and into the hollow center of each fiber. Diffusion can occur passively, although preferably by means of the external negative pressure applied within the hollow center of the fibers by means of the pump 15 (FIG. 1) operating on the plasma exit tube 12.

The number and length of fibers 20 for use with the plasma separation apparatus 10 depends on the plasma flow rate required for the dialysis apparatus. For a flow rate of 7.5 ml/min, a nominal 120 cm$^2$ surface area of the plasma separation fibers 20 is required. Referring to FIG. 2 where A denotes the length of each individual loop of fiber 20 when elongated so that the two sides of the loop are substantially parallel with each other, and where B denotes the overall diameter of the bundle of fibers as thus elongated, this surface area is provided by fifty loops of fibers 120 microns in diameter, with length A = 2.68 inches and diameter B = 0.18 inches.

It should be evident that other configurations of fibers may be provided which meet the overall surface area requirements mentioned herein, and that other surface areas and plasma flow rates may be appropriate for the needs of other patients.

Referring again to FIG. 1, the dialysis apparatus 13 includes a pressure transducer 40 responsive to the pressure of plasma flowing through the plasma exit tube 12 to the pump 15. A second pressure transducer 41 is located in the plasma line 44 downstream from the pump 15. The pressure transducers 40 and 41 provide pressure-responsive signals to the controller 42. The signals from the pressure transducers 40 and 41 together evaluate the pressure drop across the pump 15 and can determine the back pressure caused by the remainder of the plasma loop to the patient. This back pressure can detect unsafe conditions such as a blockage or open circuit in the plasma loop which includes the plasma separation apparatus 10 and the dialysis apparatus 13.

The plasma line 44 extends from the pump 15 to the dialyzer assembly 46. This dialyzer assembly includes a hollow fiber microporous membrane 47 made of cellulose or other suitable material having a pore size sufficient to allow the toxic metabolic waste in the plasma to diffuse through the pores but not sufficient to allow other plasma components to diffuse therethrough, as known to those skilled in the art, and a disposal plastic bag 48 filled with dialysate fluid 49. The membrane 47 is immersed in the dialysate fluid 49. The fiber membrane 47 typically has a pore size of about 0.015 to 0.003 $\mu$m. The outlet side of the hollow fiber membrane 47 is connected to a variable resistance valve 52 which is adjustable to control a differential pressure gradient across the membrane. Control inputs for determining that differential pressure gradient are provided by the pressure transducer 41 on the line 44 conducting plasma to the input side of the membrane, and the volume sensor 53 on the bag 48. The function of the volume sensor 53 is provided by a strain gage weight sensor responsive to the weight of the bag 48.

A sample port 56 is located downstream from the variable resistance valve 52 and provides a means of obtaining a post-dialysis sample for sending to a dialysis center to assay for assessing the progress of a patient on the system and to aid in the patient's prescription. The plasma return line 57 extends from the sample port 56 to the plasma return tube 14 associated with the plasma separation apparatus 10.

The described dialysis system operates in the following manner. Plasma from the in vivo separation apparatus 10 passes through the exit tube 12 from the proximal header 28 and flows to the dialyzer assembly 46 at a rate determined by the pump 15. As plasma is pumped through the hollow fiber membrane 47 of the dialyzer, the plasma is dialyzed by diffusion with the dialysate fluid 49 which contacts the outer surface of the membrane. This diffusion causes the metabolic waste products carried by the plasma to diffuse outwardly through the hollow fiber membrane 47 and enter the dialysate within the bag 48. When the concentration of waste products in the dialysate approaches equilibrium with the metabolic waste products carried by the plasma entering the hollow fiber membrane 47, the bag 48 is emptied by the patient and refilled with new dialysate.

Ultrafiltration or water removal from the plasma is controlled by the pump 15 and the setting of the variable resistance valve 52, which control the differential pressure gradient across the hollow fiber membrane 47. Control inputs are provided by the fluid pressure of plasma entering the dialyzer assembly 46 as measured by the pressure transducer 41 downstream from the pump 15, and by the volume sensor 53 responsive to the hydraulic pressure exerted on the bag 48.

The makeup of the dialysate 49, the hollow fiber membrane 47, and the desired operating parameters including differential pressure gradient across the hollow fiber membrane all are known to those skilled in the art and are not repeated herein. The rate of plasma flow through the dialyzer assembly 46 is determined by operation of the pump 15 and by the available flow rate of plasma from the plasma separation apparatus 10, as mentioned above. The operating parameters including flow rate, pressure drop across the pump 15, and differential pressure gradient across the hollow fiber membrane 47 are prescribed for the individual patient by a physician. For apparatus embodying the present invention and intended for use by patients themselves under a physician's prescription, it is preferred that the pump 15 receive control commands from the controller 42 which accepts inputs from the pressure transducers 40 and 41 and the volume sensor 53. The controller 20 is microprocessor-based and accepts manual inputs from the physician or a dialysis center, in addition to the measured operating parameters mentioned above. The controller is programmed to operate the pump 15 at a speed to produce the desired operating results specified by physician input in view of the feedback signals from the pressure transducers and the volume sensor. The controller 42 may also log these data and transmit periodic performance reports via the modem 60 and a telephone link to a remote dialysis center. The controller 42 optionally may accept information from the remote dialysis center which permits changing the patient's prescription for operation of the dialysis apparatus.

FIG. 5 shows a dialysis apparatus 13' which includes dialysate regeneration apparatus but which otherwise functions in the same manner as the dialysis apparatus 13 shown and described with regard to FIG. 1. The dialysis apparatus 13' has a regeneration loop 65 including a pump 66 which withdraws dialysate from the bag 48 and pumps the dialysate through the three-compartment regeneration cartridge 67. The dialysate pumped into the cartridge 67 from the bag 48 contains waste products removed from the plasma, and these waste products are removed by absorption while passing through the three compartments of the regeneration cartridge 67. The compartments A, B, and C respectively contain urease, a zeolite, and an electrolyte equilibrium such as H$^-$, Ca$^{--}$, and K$^-$. The regenerated dialysate is pumped back into the bag 48 through the outlet line 68 of the regeneration loop 65.

A pH sensor 71 in the outlet line 68 monitors the acid-base balance of the regenerated dialysate and provides a control signal to the controller 42 to regulate the bypass valve 71 which regulates the proportion of dialysate flow through path ACB as compared with path AB, thus controlling the electrolyte balance of the regenerated dialysate. The pressure transducer 72 monitors the fluid pressure in the outlet line 68 of the regeneration loop, and provides a feedback signal to the controller 42' which regulates the command control speed of the pump 66 in the regeneration loop. A waste valve 75 on the bag 48 permits manual removal of ultrafiltrated water from the dialysate apparatus in excess of the needs of the system.

The controller 42' also controls operation of the pump 15 delivering plasma to the dialyzer assembly 46' in the manner described above with reference to FIG. 1. The speed of the pump 15 is determined by the physician's prescription for a particular patient, and is based on feedback signals from the pressure transducers 40 and 41 and the volume sensor 53 repsonsive to the weight of fluid in the bag 48.

It should be understood that the foregoing relates only to preferred embodiments of the present invention, and that numerous changes and modifications therein may be made without departing the spirit and scope of the invention as defined in the following claims.

We claim:

1. An apparatus for kidney dialysis using in vivo separation of plasma from blood and extracorporeal separation of toxic metabolic waste from the separated plasma, comprising:

at least one elongated micorporous fiber having a hollow interior, said fiber being dimensioned to be received within a blood vessel without significantly obstructing fluid flow through said blood vessel, the pore size of the fiber being sufficient to allow plasma to diffuse through the pores into the hollow interior of the fiber but not sufficient to allow cellular components larger than plasma to diffuse therethrough;

the hollow interior of said elongated fiber being in fluid communication with a means for conducting plasma comprising a first hollow tube which connects to the hollow interior of the fiber and permits passage of plasma to said blood vessel;

extracorporeal dialysis means receiving the plasma passing through the first tube and removing toxic metabolic waste from the plasma; and means conducting the plasma from the extracorporeal dialysis means to the second hollow tube for return to the blood vessel.

2. Apparatus as in claim 1, further comprising a pump for moving the plasma to the extracorporeal dialysis means from the first hollow tube.

3. Apparatus as in claim 1, wherein the fiber is composed of a polymeric material having a pore size of from about 0.1 to 1.0 μm.

4. Apparatus as in claim 1, wherein the fiber is composed of a polymeric material having a pore size of about 0.2 to 0.8 μm.

5. Apparatus as in claim 1, wherein the fiber is composed of a polymeric material having a pore size of about 0.4 to 0.6 μm.

6. Apparatus as in claim 1, wherein the extracorporeal dialysis means comprises at least one hollow fiber of polymeric material having pore size sufficient to allow the toxic metabolic waste in the plasma to diffuse through the pores but not sufficient to allow other plasma components to diffuse therethrough.

7. Apparatus as in claim 4, wherein the fiber of the extracorporeal dialysis means has a pore size of about 0.0015 to 0.003 μm.

8. An apparatus for continuous in vivo separation of plasma from blood and extracorporeal dialysis of the plasma, comprising:

a primary filter comprising at least one elongated microporous fiber having a hollow interior and dimensioned to fit within a blood vessel;

the pore size of the fiber being sufficient to allow plasma to diffuse through the pores into the hollow interior but not sufficient to allow cellular components larger than plasma to diffuse therethrough;

means comprising a first hollow tube connected to the primary filter to receive the plasma from the interior of the fiber;

an extracorporeal secondary filter connected to receive the plasma passing through the first tube and operative to remove toxic metabolic waste from the plasma; and means comprising a second hollow tube connected to return the plasma from the extracorporeal secondary filter to a blood vessel.

9. The apparatus as in claim 8, wherein:

the primary filter includes a header dimensioned to fit within the first-mentioned blood vessel without substantially obstructing fluid flow through the blood vessel;

the fiber extends outwardly from the header within the blood vessel;

the first hollow tube is in fluid flow communication with the header to remove the plasma from the blood vessel; and the second hollow tube is in fluid flow communication with the header to return the plasma from the extracorporeal dialysis means to said blood vessel.

10. An apparatus for kidney dialysis using in vivo separation of plasma from blood and extracorporeal separation of toxic metabolic waste from the separated plasma, comprising:

a primary filter comprising a microporous membrane dimensioned to be received within a blood vessel without significantly obstructing fluid flow through said blood vessel, the pore size of the membrane being sufficient to allow plasma to diffuse through the pores but not sufficient to allow cellular components larger than plasma to diffuse therethrough;

plasma collection means in fluid communication with the membrane and having a hollow tube which conducts plasma from the primary filter;

extracorporeal dialysis means connected to receive the plasma passing through the tube and removing toxic metabolic waste from the plasma; and means conducting the plasma from the extracorporeal dialysis means for return to a blood vessel.

11. A method for continuous kidney dialysis using plasma in lieu of blood, comprising the steps of:

implanting in a blood vessel at least one elongated microporous fiber having a hollow interior and dimensioned to be received within a blood vessel without significantly obstructing fluid flow through the blood vessel, the pore size of the elongated microporous fiber being sufficient to allow plasma to diffuse through the pores into the hollow interior of the fiber but not sufficient to allow cellular components larger than plasma to diffuse therethrough;

placing the hollow interior of said elongated fiber in fluid communication with a means for conducting plasma comprising a first hollow tube which connects to the hollow interior of the fiber and permits passage of plasma from the fiber, and a second discrete tube which returns plasma to said blood vessel;

removing plasma from the blood vessel;

treating the removed plasma to remove toxic metabolic waste from the plasma; and re-infusing thne plasma into the blood vessel.

* * * * *